(12) United States Patent
Ball et al.

(10) Patent No.: US 6,364,486 B1
(45) Date of Patent: Apr. 2, 2002

(54) METHOD AND APPARATUS FOR TRAINING VISUAL ATTENTION CAPABILITIES OF A SUBJECT

(75) Inventors: Karlene K. Ball, Hoover, AL (US); Kristina K. Berg, Chicago, IL (US)

(73) Assignee: Visual Awareness, Inc., Chicago, IL (US)

( * ) Notice: Subject to any disclaimer, the term of this patent is extended or adjusted under 35 U.S.C. 154(b) by 0 days.

(21) Appl. No.: 09/743,846

(22) PCT Filed: Apr. 9, 1999

(86) PCT No.: PCT/US99/07926

§ 371 Date: Jan. 12, 2001

§ 102(e) Date: Jan. 12, 2001

(87) PCT Pub. No.: WO99/52419

PCT Pub. Date: Oct. 21, 1999

Related U.S. Application Data (60) Provisional application No. 60/081,289, filed on Apr. 10, 1998.

(51) Int. Cl.[7] .................................................. A61B 3/00
(52) U.S. Cl. ....................................................... 351/203
(58) Field of Search ................................. 351/203, 211, 351/224, 237, 243, 246; 482/902

(56) References Cited

U.S. PATENT DOCUMENTS

| 4,447,141 A | 5/1984 | Eisenkraft |
| 4,971,434 A | 11/1990 | Ball |
| 5,469,740 A | 11/1995 | French et al. |
| 5,589,897 A | * 12/1996 | Sinclair et al. ............. 351/237 |
| 5,801,810 A | 9/1998 | Roenker |

FOREIGN PATENT DOCUMENTS

EP 0 411 821 A1 * 7/1990

* cited by examiner

Primary Examiner—George Manuel
(74) Attorney, Agent, or Firm—Brinks Hofer Gilson & Lione (57) ABSTRACT

A system for training the visual attention capabilities of a subject presents a series of sets of tests to the subject on a conventional touch screen monitor. Each test includes a central target, a peripheral target and distractor elements around the peripheral target. The display time for the displays and the eccentricity of the peripheral target are held constant within each set of tests. When the subject reaches a desired level of success in identifying the central target and in locating the peripheral target, eccentricity of the peripheral target is increased for the next set of tests. Once eccentricity reaches a maximum value, display time is decreased and eccentricity is decreased for the next set of tests.

27 Claims, 5 Drawing Sheets

METHOD AND APPARATUS FOR TRAINING VISUAL ATTENTION CAPABILITIES OF A SUBJECT

This application is a 371 of PCT/US99/07926 filed Apr. 10, 1998 which claims benefit of Provisional Ser. No. 60/081,289.

This patent document makes reference to an appendix which includes a program listing. This listing is subject to copyright protection. The copyright owner has no objection to the facsimile reproduction by anyone of this listing, as it appears in the Patent and Trademark Office files and records, but reserves all other copyright rights whatsoever.

BACKGROUND

This invention relates to systems and methods for training or improving the visual attention capabilities of a subject.

Ball U.S. Pat. No. 4,971,434, assigned to the assignee of the present invention, describes an efficient and reliable method for diagnosing deficiencies in a subject's Useful Field of View (the UFOV® parameter). As described in detail in the Ball patent, a series of visual displays are presented to the subject, who is asked to identify a foveal target and in some tests to locate a peripheral target. The peripheral target is positioned at varying radial distances from the foveal target and at varying angular positions. In some displays the peripheral target is embedded in a field of distractor elements.

The UFOV® parameter is defined as the spatial area or visual field extent that is needed for a specific visual task. As explained in the Ball patent, measurements related to the UFOV® parameter can be used in diagnosing deficiencies in a subject's visual attention capabilities.

At columns 12 and 13 of the above-identified Ball patent, various modes are discussed to improve the visual attention capabilities of a subject. In each of the three modes, the UFOV® parameter is calculated, and changes in the displayed visual tests are made based on the value of the UFOV® parameter. As explained previously in the Ball patent, calculation of the UFOV® parameter entails displaying multiple visual tests at a common display time and varying peripheral target eccentricities. Thus, for example, three different values of peripheral target eccentricity can be used for each respective display time to allow calculation of the UFOV® parameter.

Another prior art visual attention training program is disclosed in a thesis authored by Lauren M. Jackson "The Effects of Decreased Uncertainty and Telescopic versus Full Field Training on the Useful Field of View" at pages 38–41. In this document, a set of visual tests is defined including a central task, a peripheral target and a display duration. Eccentricity of the peripheral target is then increased when the subject displays a selected level of accuracy in identifying the central target and locating the peripheral target. However, the display time is never altered in the training mode disclosed by Jackson.

The present invention is directed to an improved training method and apparatus that avoids the need to calculate the UFOV® parameter, and that varies both display time and eccentricity to provide effective training of the subject.

SUMMARY

The present invention is defined by the following claims, and nothing in this section should be taken as a limitation on those claims. By way of introduction, the preferred embodiments described below present a subject with multiple sets of visual tests. Each test includes at least one of the following elements: a central target, a peripheral target, and a set of distractor elements. First and second difficulty parameters are held constant within each set. When the subject achieves a desired success rate for two successive sets, the difficulty of at least a first one of the difficulty parameters is increased for the next set up to a maximum value. When the subject achieves the desired success rate for two successive sets and the first difficulty parameter is at the maximum difficulty, then the difficulty of at least the first difficulty parameter is reduced for the next set of tests and the difficulty for at least the second difficulty parameter is increased for the next set of tests.

DETAILED DESCRIPTION OF THE PRESENTLY PREFERRED EMBODIMENTS

Figure 1:
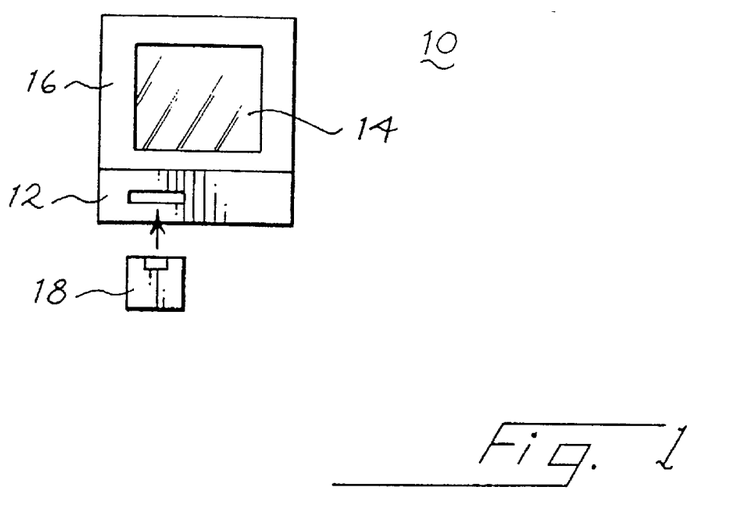
FIG. 1 is a block diagram of a computer system that can be used to implement the present invention.

Turning now to the drawings, FIG. 1 shows a computer system 10 which incorporates a presently preferred embodiment of this invention. The computer system 10 includes a conventional central processor 12 that responds to a touch screen 14 and presents visual displays on a monitor 16. The central processor 12 can read and write data on a computer-readable storage device 18.

The components 10–18 are conventional, and do not per se form part of this invention. Simply by way of example, the central processor 12 can be a conventional PC compatible computer, the touch screen 14 can be a conventional device, monitor 16 can be a conventional 17-inch CRT, and the storage device 18 can be a conventional hard disk, floppy disk, or a CD-ROM disc. Many other input devices may be substituted for the touch screen 14, including a joystick, a keyboard, a mouse, a track ball, or a voice-recognition system. As described below, some embodiments of this invention rely on manual evaluation, in which case the input device may not be required. Also, any suitable display device can be used, including video systems and projected image systems.

Figure 2:
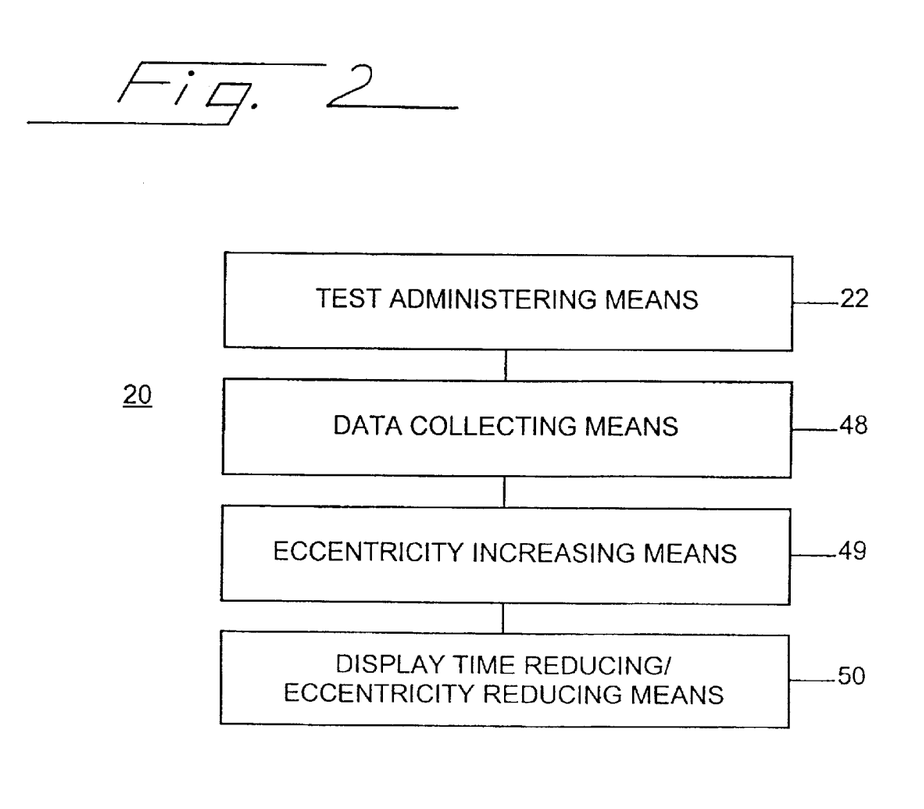
FIG. 2 is a block diagram of a computer program included in the system of FIG. 1.

As shown in FIG. 2, the computer system 10 executes a program 20 that may, for example, be stored on the storage device 18. The program 20 includes four basic subroutines or systems. The first of these is a test administering means 22. As described below, the test administering means 22 displays multiple sets of visual tests. Each test within a set can take the general form shown in FIG. 3. In FIGS. 3–7, images are shown as black lines on a white background. This has been done for clarity of illustration; in actual practice, the background is generally dark and the images are generally displayed as bright lines, though the reverse can be used. The background and/or the visual elements may be displayed in any desired colors.

Figure 3:
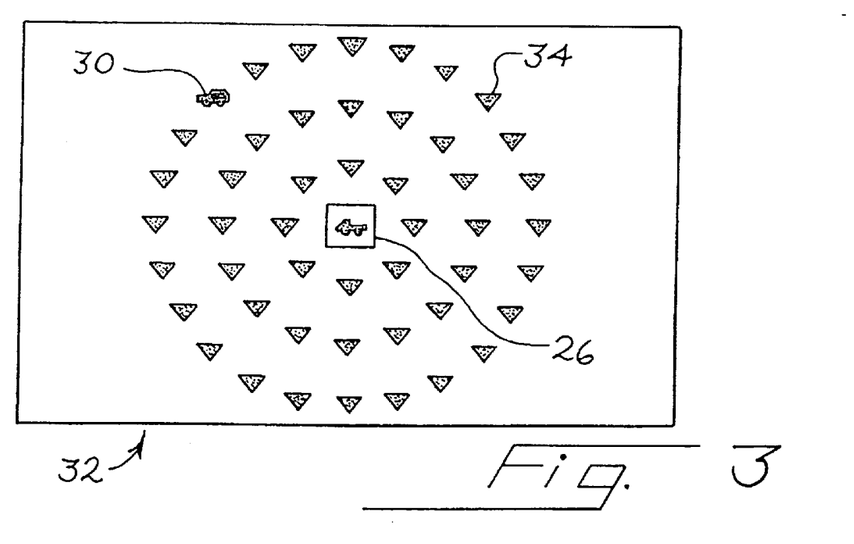
FIG. 3 is an illustrative view of a visual display suitable for use in the program of FIG. 2.

The visual display 32 of FIG. 3 includes a foveal or central target 26 and a peripheral target 30. The foveal target 26 can take any one of a number of visually distinct patterns or forms, and one of these forms is selected for each visual display 32 of a set. The peripheral target 30 can be positioned at any one of a number of separate visual eccentricity angles (such as 10, 20 or 30° with respect to the foveal target 26), and the peripheral target 30 can be positioned at any one of a number of angular positions with respect to the foveal target 26, such as those illustrated in FIG. 7. Of course, the peripheral target 30 can also take any of several different patterns or forms, depending upon the application. Within any set of displays, the identity of the foveal target and the angular location of the peripheral target will be varied randomly, pseudo randomly, or according to a stored list from test to test. Additionally, the display 32 also includes an array of distractor visual elements 34 which may take any desired form, and which may vary within a sequence. The peripheral target 30 is embedded in the distractor elements 34, which increase the difficulty of locating the peripheral target 30.

Figure 4:
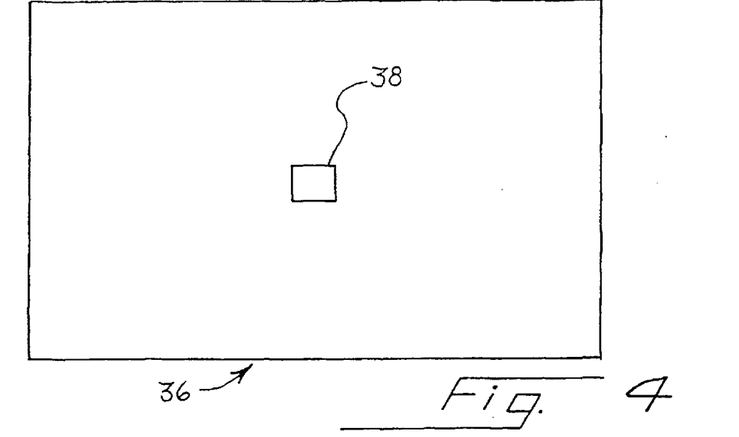
FIGS. 4, 5, 6 and 7 are schematic views of a fixation image, a mask image and first and second response images, respectively, suitable for use in the program of FIG. 2.

Preferably, each time the display 32 is displayed, it is preceded by a fixation display 36 as shown in FIG. 4. This fixation display includes a fixation image 38 aligned with the foveal target 26 described above. The subject is asked to focus his or her vision on the fixation image 38 in order to provide a consistent starting point for viewing of the subsequent display 32. Alternatively, the fixation display can be deleted from the tests.

Figure 5:
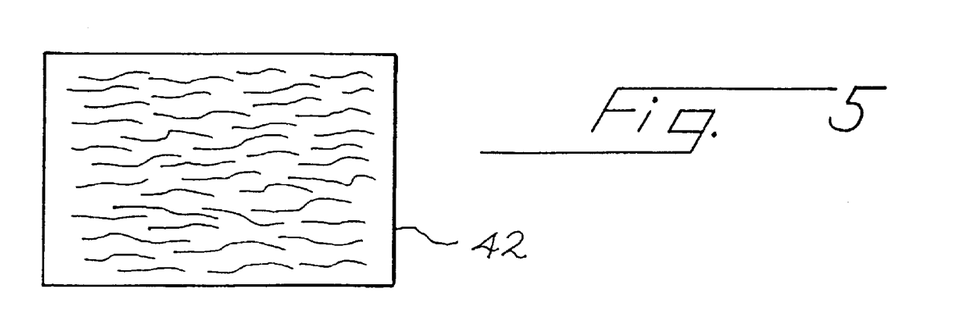

After the display 32 has been removed, it is preferably immediately followed by a mask image 42 (FIG. 5). The purpose of the mask image is to terminate display of the image 32 at a repeatable time, and to eliminate any retinal after-images that might effectively prolong the display time of the preceding display 32. Alternatively, the mask image can be deleted from the tests.

Figure 6:
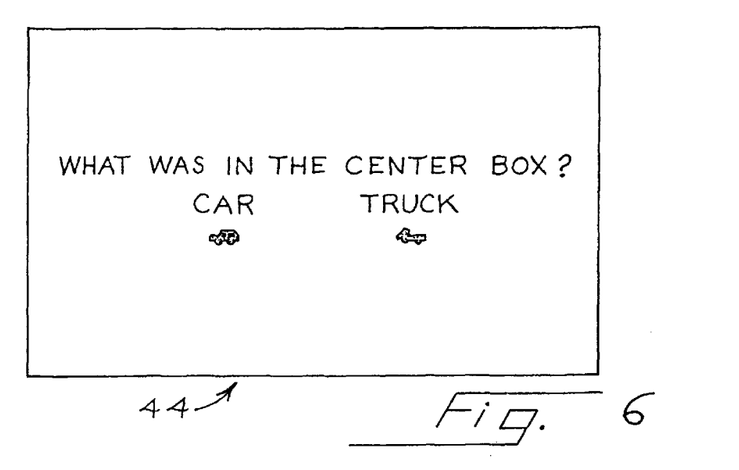
Figure 7:
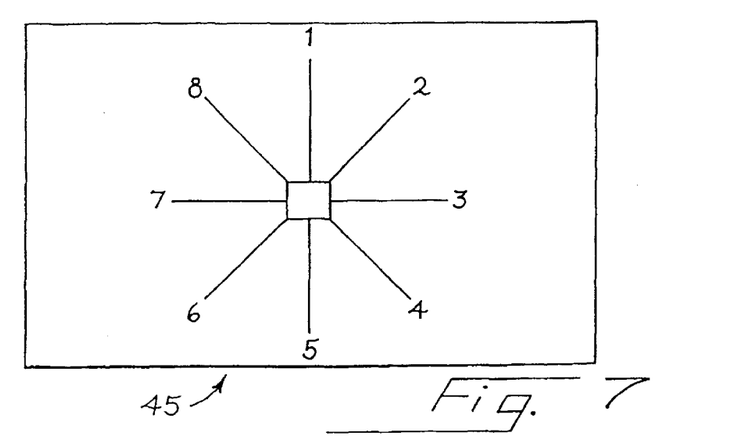

Following the mask image 42, one or more response images 44, 45 may be displayed if desired (FIGS. 6 and 7). The response image 44 may be used to prompt the subject to identify the foveal target. The response image 45 includes a number of radiating lines, for example eight lines oriented and numbered as shown. The response image 45 may be used to assist the subject in selecting the number of the line that most closely corresponds to the angular position of the peripheral target 30 on the preceding visual display 32. Alternatively, the response images may be varied or deleted from the tests.

Once the display 32 has been shown for the designated display time, the program 20 of FIG. 2 then collects user responses with a data collecting means 48. For example, the subject may be asked to enter responses into the computer system 10 directly with the touch screen 14. Of course, the number of peripheral target angular positions and the number of central target alternatives can be modified as desired. For example, the touch screen or the keys of a conventional numeric keypad may be marked to assist the subject in entering responses. Alternately, the subject can call out his or her responses (identification of the foveal target 26 and angular location of the peripheral target 30), and a test administrator can enter the responses via the touch screen 14. As yet another alternative, the subject can call out his or her responses, the test administrator can record these responses in any suitable manner, and the test administrator can enter the recorded responses into the computer system 10 after all the displays of a set have been presented. For example, the data collecting means 48 can include software for prompting the test administrator to enter the previously-recorded responses, or the previously-recorded responses can be supplied via disk or other storage medium. Other alternatives include voice recognition systems which facilitate the entry of responses either by the subject or by a test administrator. Also, the test administrator may record and assess the subject's responses, without computer assistance; in such embodiments the data collecting means can be deleted. As used herein, a user response which locates the peripheral target may specify only its approximate location, and a user response which identifies the foveal target may do so by selecting one of a few alternatives.

As described in the examples below, each set of visual displays generated by the means 22 preferably displays all of the peripheral targets 30 at the same eccentricity and for the same display time, and the program 20 quickly provides a pass/fail indication after a number of visual displays have been presented to the subject. Alternatively, the eccentricity and/or display time can be varied within a set. The program includes means 49 for increasing peripheral target eccentricity between sets up to a maximum eccentricity and means 50 for reducing both eccentricity and display time between sets as described below.

Figure 8:
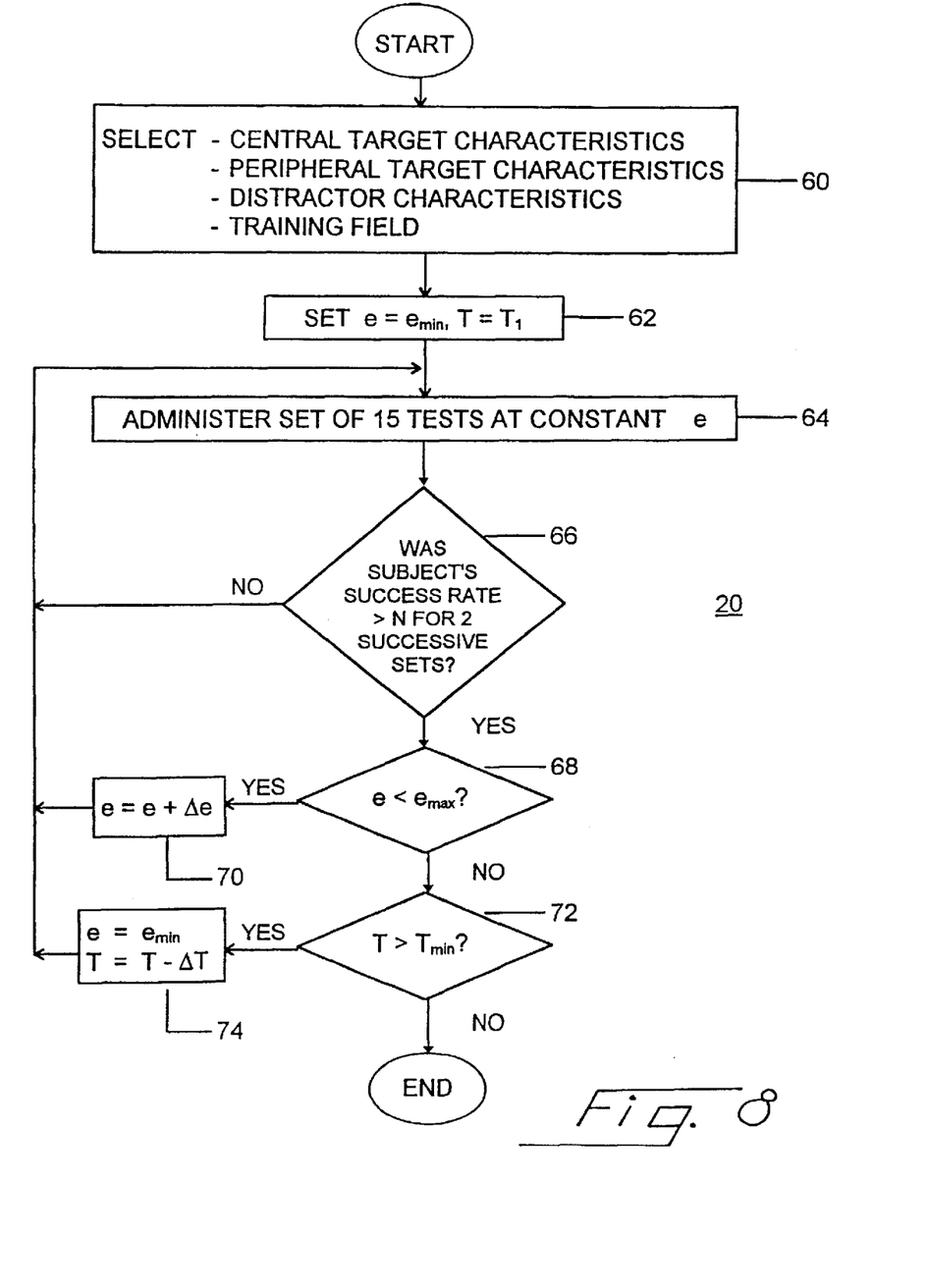
FIG. 8 is a flow chart of a preferred embodiment of the program of FIG. 2.

FIG. 8 shows a flow chart of a first version of the program 20. The first step 60 in the program of FIG. 8 is a setup routine that prompts the test administrator to select the difficulty of the test. For example, the characteristics of the central target, the peripheral target, and the distractor elements can all be selected as desired. If the available central targets are relatively similar to one another, the resulting tests are relatively difficult. Similarly, if the peripheral targets are matched in brightness to the distractor elements, the tests are also relatively difficult. Various difficulty parameters can be modified to achieve the desired results, as for example one or more of the following characteristics of the visual elements of the display: shape, size, color, brightness, presence/absence, form, location, and orientation. Also, the test administrator can select the training field. If a particular subject has a visual attention deficit in only a certain visual region (such as the right half of the visual field), training can be concentrated in that region.

After the initial setup, the program then sets peripheral target eccentricity e to a minimum value $e_{min}$ and sets the display time T to an initial value T1. T1 can be selected based on the subject's performance in tests of visual attention capabilities.

The program of FIG. 8 then administers a set of a selected number of tests at the initially selected display time and peripheral target eccentricity. In this example there are 16 tests in each set, though this number can be varied as desired. In each test, displays of the type shown in FIGS. 3, 4 and 5 are shown to the subject. Then the subject is prompted to identify the central target using the screen of FIG. 6 and to locate the peripheral target using the screen of FIG. 7. Step 64 assesses the subject's accuracy in identifying the central target and in locating the peripheral target for each of the tests within the set of tests being conducted.

In block 66 the program determines whether the subjet's success rate was greater than a predetermined threshold for two successive sets of tests. For example, a success rate of 75% accuracy can be used, where accuracy is defined as both correctly identifying the central target and correctly locating the peripheral target for a single test. If the subject has not met the selected success rate for two successive sets, control is returned to step 64, without changing the eccentricity or display time. Once the subject has met the desired success rate for two successive sets, the program then tests the current value of eccentricity to determine whether it is less than the maximum value of eccentricity permitted by the program. If so, eccentricity is increased (thereby making the next set of visual tests more difficult), and control is returned to step 64. At this stage, the display time T has not been changed.

Once the subject reaches the desired success rate for two successive sets and the eccentricity is no longer less than the maximum eccentricity, the program then tests the display time T in block 72 to determine whether T is greater than a minimum display time $T_{min}$. If so, the program decreases the display time T and simultaneously decreases the eccentricity for the next set of tests before returning control to step 64. Reducing the display time increases the difficulty of the next set of visual tests, while reducing the eccentricity reduces the difficulty of the next set of tests. In this way, an effective transition is provided between sets of tests. This transition has been found to provide a high rate of training.

Once the subject reaches the required success rate for two consecutive sets of tests, the eccentricity is at $e_{max}$ and the display time is at $T_{min}$, the training program of FIG. 8 ends.

The specific example of FIG. 8 can readily be varied. For example, the display time and the eccentricity are not required to be strictly constant within a set of tests. Rather, the average display time and the average eccentricity may be varied between one set and another while permitting variance of display time and/or eccentricity within any given set of tests. The required success rate can be greater or less than the example of 75% indicated above, and the number of successive sets of tests for which the subjet's success rate is required to better than the predetermined level can be greater or less than two.

Attached Appendix A provides a listing of a presently preferred embodiment of the program of FIG. 8. The program listed in Appendix A may be executed on a variety of IBM PC compatible computers of the following type: Pentium-133 MHz processor with a 2MB VGA video card and a 17-inch VGA color touch screen monitor using a DOS operating system. Of course, this embodiment can readily be adapted for other computers, including Macintosh and others.

The foregoing detailed example of FIGS. 1 through 8 represents only one of many implementations of the present invention. It should be recognized that many alternatives are possible. For example, this invention can be used in training programs that use visual tests with images that differ from that of FIG. 3. In one alternative the central target 26 and the peripheral target 30 are included, but the distractor elements 34 are deleted. In another variation the central target 26 is included but both the peripheral target 30 and the distractor elements 34 are deleted. In yet another alternative the central task posed to the subject differs from that described above. Instead of identifying the central target 26, the subject can be asked to determine the presence or absence of the central target, or to determine whether two simultaneously displayed central targets are the same or different. As yet another alternative, multiple peripheral targets can be used and the peripheral target task can be varied.

Figure 9:
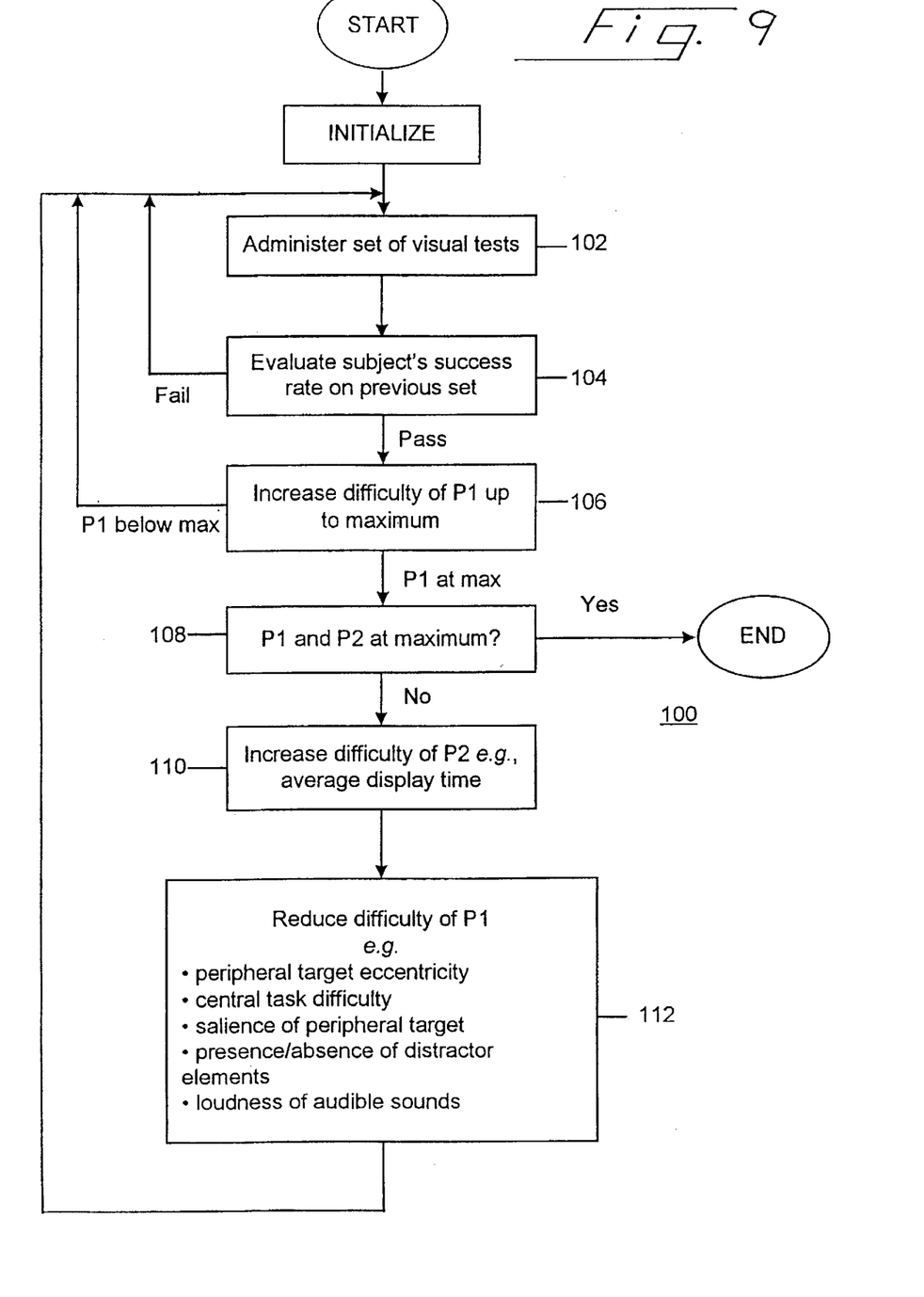
FIG. 9 is a flow chart of another preferred embodiment of the method of this invention.

FIG. 9 provides a flow-chart of a method 100 that will be used to describe other embodiments of this invention. The first step 102 of the method of FIG. 9 is to administer multiple sets of visual tests including first and second consecutive sets. The visual tests within these sets will in general include one or more of the following visual elements: a central target which may be similar to the central target 26 of FIG. 3, a peripheral target which may be similar to the peripheral target 30 of FIG. 3, and a set of distractor elements which may be similar to the distractor elements 34 of FIG. 3. Thus, any of the visual tests can include one, two or all three of these visual elements. Each of the sets of visual tests administered in step 102 is characterized by respective first and second difficulty parameters P1 and P2. The term "difficulty parameter" is intended broadly to encompass any parameter of the test that affects the visual attention difficulty of the test. The first and second difficulty parameters can include for example any of the following parameters.

1. Display time—As discussed above, reduced display time is associated with increased difficulty.
2. Peripheral target eccentricity—As explained above, increased peripheral target eccentricity is associated with increased difficulty.
3. Central task difficulty—The central task can be made more or less difficult depending upon the shape, size, color, brightness, presence/absence, form, location, orientation or number of central targets and the information required of the subject regarding the central target (i.e., identification of the central target or determination whether two central targets are identical or dissimilar).
4. Peripheral task difficulty—The peripheral task (if present) can be made more or less difficult by altering the shape, size, color, brightness, presence/absence, form, location, orientation or number of the peripheral targets with respect to distractor elements (if present).
5. The presence or absence of distractor elements—Distractor elements, when present, increase the difficulty of the associated test.
6. The presence or absence of audible sounds or the loudness of audible sounds—Audible sounds presented to the subject during a test increase the difficulty of the test.

Depending upon the visual elements in a particular visual test, selected ones of the above-referenced difficulty parameters, as well as other difficulty parameters, will be relevant.

In step 104 of FIG. 9, the subject's success in recognizing selected visual features of the set of tests is evaluated. The nature of the evaluation will depend upon the test, and may include evaluation of the subjects success at one or more of the following tasks: (1) identifying the central target, (2) locating the peripheral target, (3) detecting the presence or absence of a central target, (4) detecting the identity or dissimilarity of two central targets. Other evaluations of the subject's success can be used depending upon the test used. If the evaluation of step 104 concludes that the subject has not reached the desired success rate, control is returned to step 102 and training is resumed without change of the difficulty parameters P1, P2. Alternately, if the subject has reached the desired success rate in a first set of visual tests the first parameter P1 is then made more difficult in step 106 up to a maximum. If P1 is below a maximum value, control is returned to step 102 and training is resumed with the more difficult value of P1 and the previous value of P2. If P1 is at a maximum value, P2 is assessed in step 108 to determine whether it too is at maximum difficulty. If so, the training program ends. Otherwise, control is transferred to step 110.

In step 110 the difficulty of the second difficulty parameter P2 is increased for the second set as compared with the first set, and in step 112 the difficulty of the first difficulty parameter P1 is reduced for the second set as compared to the first set. After step 112 control is returned to step 102 and training is resumed with the revised parameters P1, P2. For example, the second difficulty parameter P2 can be any of a wide variety of aspects of the tests, including for example central task difficulty, peripheral target eccentricity, peripheral target salience, distractor element presence, or audible sound presence or loudness. The first difficulty parameter P1 can be any of a wide variety of aspects of the tests, including for example central task difficulty, peripheral target eccentricity, peripheral target salience or number, distractor element presence, or audible sound presence or loudness. The second parameter P2 may also be the average display time, and the difficulty of the average display time parameter can be increased in step 110 by reducing the average display time for the next set of visual tests.

It will be recognized that the method 100 of FIG. 9 increases the difficulty of the second difficulty parameter P2 and reduces the difficulty of the first difficulty parameter P1 in the transition between two consecutive sets of visual tests. This approach has been found to provide an effective training algorithm.

The difficulty parameters P1, P2 can be varied either automatically or manually to implement the method 100 of FIG. 9. For example, a suitably programmed computer can operate to alter the parameters P1, P2 as discussed above. Alternately, a test administrator can implement this algorithm manually.

The preferred embodiments described above provide important advantages. In clinical testing, these embodiments have been found to provide particularly effective training of a subject, allowing the subject to improve his or her visual attention capabilities quickly. Since the UFOV® parameter is not calculated for each display time, there is no need to provide tests at multiple eccentricities for a given display time. The training method described above may be performed on a small computer monitor without the use of a chin rest. This results in reduced precision, but it reduces hardware requirements and simplifies use of the system in a setting such as a physician's office or training facility. When the test administrator enters the subjet's test responses, there is no need for a special mechanism such as a keyboard, joystick, touch screen or the like which may be needed to allow the subject to enter responses without assistance.

As pointed out in connection with FIGS. 8 and 9, in many cases two consecutive sets of visual tests are administered using the same first and second difficulty parameters (e.g., display time and eccentricity). In these embodiments, it is only when the subject demonstrates an adequate level of performance and one of the parameters is at maximum difficulty that the first and second difficulty parameters are changed in opposite directions between the first and second sets of tests.

As used herein, the term "first and second consecutive sets" is intended broadly such that the first set can follow the second set or vice versa.

Of course, it will be recognized that a wide range of changes and modifications can be made to the preferred embodiments described above. For example, the particular algorithm used to train the visual attention capability of the subject can be varied widely, and any suitable hardware and software routines can be used to implement the methods and systems described above. The central target may be positioned off-center on the monitor (as long as it is aligned with the point of gaze of the subject), and the figures used for the central target, the peripheral target and the distractors may be varied as desired. It is not essential in all embodiments that distractor elements be provided in the visual tests. In the case of subjects with compromised visual attention systems, useful training may be performed using either a central target and a peripheral target or a central target only while eliminating all distractor elements.

The central and peripheral targets can be provided with any suitable form, and if desired they can be abstract forms represented by appropriately shaped dots of light or darkness.

The embodiments described above have included a single peripheral target and a single central target within each display. It will be appreciated that if desired multiple central targets and/or multiple peripheral targets can be used in a single display.

In some embodiments, the difficulty parameters may be varied according to a pre-programmed schedule, rather than in response to the accuracy of the training responses. For example, a video tape or a pre-programmed sequence or schedule of images can be prepared using a standard progression of sets of visual tests that employ difficulty parameters that are varied as described above. In these embodiments, valuable training is provided in a low-cost manner.

It is therefore intended that the foregoing detailed description be regarded as an illustration of preferred forms of the invention and not as a limitation of the invention. It is only the following claims, including all equivalents, which are intended to define the scope of this invention.

What is claimed is:

1. A method for training visual attention capabilities of a subject, said method comprising the following steps:
   (a) administering a plurality of sets of visual tests to the subject; each set characterized by first and second difficulty parameters; each test comprising at least one visual element selected from the group consisting of: a central target, a peripheral target, and a set of distractor elements; said plurality of sets comprising consecutive first and second sets;
   (b) reducing difficulty of the first difficulty parameter for the second set as compared with the first set; and
   (c) increasing difficulty of the second difficulty parameter for the second set as compared with the first set.

2. The method of claim 1 wherein each test comprises both a respective central target and a respective peripheral target, and wherein step (b) comprises the step of
   altering an average peripheral target eccentricity for the second set as compared with the first set.

3. The method of claim 1 wherein step (b) comprises the step of altering at least one of presence/absence and loudness of an audible sound during the first set as compared to the second set.

4. The method of claim 1 wherein each test comprises a respective central target, and wherein step (b) comprises the step of altering a central task of the second set as compared to the first set.

5. The method of claim 1 wherein each test comprises a respective central target, a respective peripheral target and a respective set of distractor elements, and wherein step (b) comprises the step of:
   reducing an average peripheral target eccentricity for the second set as compared with the first set.

6. The method of claim 1 wherein each test comprises a respective central target, a respective peripheral target and a respective set of distractor elements, and wherein step (b) comprises the step of:
   altering salience of the peripheral target with respect to the respective set of distractor elements for the second set as compared to the first set.

7. The method of claim 1 wherein each test comprises both a respective central target and a respective peripheral target, and wherein step (b) comprises the step of adding distractor elements to the first set as compared to the second set.

8. The method of claim 1, 2, 3, 4, 5, 6 or 7 wherein step (b) comprises the step of reducing an average display time for the second set as compared with the first set.

9. The method of claim 1 wherein the plurality of sets of visual tests of step (a) are administered in a pre-programmed sequence.

10. A method for training visual attention capabilities of a subject, said method comprising the following steps:
   (a) administering a plurality of sets of visual attention tests to the subject; each set characterized by first and second difficulty parameters; each test comprising at least one visual element selected from the group consisting of: a central target, a peripheral target, and a set of distractor elements; said plurality of sets comprising first and second sets;
   (b) increasing difficulty of the first difficulty parameter for the first set of tests up to a maximum difficulty when the subjet's success rate in at least one respective preceding set of tests is above a threshold level; and
   (c) reducing difficulty of the first difficulty parameter and increasing difficulty of the second difficulty parameter for the second set of tests when the first difficulty parameter is at the maximum difficulty and the subjet's success rate in at least one respective preceding set of tests is above the threshold level.

11. The method of claim 10 wherein each test comprises both a respective central target and a respective peripheral target, and wherein step (c) comprises the step of
   reducing an average peripheral target eccentricity for the second set of tests.

12. The method of claim 10 wherein step (c) comprises the step of altering at least one of presence/absence and loudness of an audible sound during the first set as compared to the second set.

13. The method of claim 10 wherein each test comprises a respective central target, and wherein step (c) comprises the step of altering a central task of the second set as compared to the first set.

14. The method of claim 10 wherein each test comprises a respective central target, a respective peripheral target and a respective set of distractor elements, and wherein step (c) comprises the step of:
   altering an average peripheral target eccentricity for the second set.

15. The method of claim 10 wherein each test comprises a respective central target, a respective peripheral target and a respective set of distractor elements, and wherein step (c) comprises the step of:
   altering salience of the peripheral target with respect to the respective set of distractor elements for the second set as compared to the first set.

16. The method of claim 10 wherein each test comprises both a respective central target and a respective peripheral target, and wherein step (c) comprises the step of
   adding distractor elements to the first set as compared to the second set.

17. The method of claim 10, 11, 12, 13, 14, 15 or 16 wherein step (b) comprises the step of reducing an average display time for the second set as compared with the first set.

18. A method for training visual attention capabilities of a subject, said method comprising the following steps:
   (a) administering a plurality of sets of visual attention tests to the subject, each test comprising a respective central target and respective peripheral target, each set characterized by an average display time and an average peripheral target eccentricity, said plurality of sets comprising first and second consecutive sets;
   (b) reducing the average display time for the second set as compared to the first set; and
   (c) reducing the average peripheral target eccentricity for the second set as compared to the first set.

19. A method for training visual attention capabilities of a subject, said method comprising the following steps:
   (a) administering a plurality of sets of visual attention tests to the subject, each test comprising a respective central target and respective peripheral target, each set characterized by an average display time and an average peripheral target eccentricity, said plurality of sets comprising first and second sets;
   (b) increasing the average peripheral target eccentricity for the first set of tests up to a maximum eccentricity when the subjet's success rate in identifying the central targets and locating the peripheral targets in a respective preceding set of tests is above a threshold level; and
   (c) reducing the average peripheral target eccentricity and reducing the average display time for the second set of tests when the average peripheral target eccentricity is at a maximum eccentricity and the subjet's success rate in identifying the central targets and locating the peripheral targets in a respective preceding set of tests is above the threshold level.

20. A system for training visual attention capabilities of a subject, said system comprising:
   means for administering a plurality of sets of visual attention tests to the subject, each test comprising a respective central target and respective peripheral target, each set characterized by an average display time and an average peripheral target eccentricity, said plurality of sets comprising first and second consecutive sets;
   means for reducing the average display time for the second set as compared to the first set; and
   means for reducing the average peripheral target eccentricity for the second set as compared to the first set.

21. A computer-readable storage medium comprising a computer program, said program comprising:
   means for administering a plurality of sets of visual attention tests to the subject, each test comprising a respective central target and respective peripheral target, each set characterized by an average display time and an average peripheral target eccentricity, said plurality of sets comprising first and second consecutive sets;
   means for reducing the average display time for the second set as compared to the first set; and
   means for reducing the average peripheral target eccentricity for the second set as compared to the first set.

22. The invention of claim 18, 19, 20 or 21 wherein the plurality of sets of visual tests of step (a) are administered in a pre-programmed sequence.

23. A system for training visual attention capabilities of a subject, said system comprising:
   means for administering a plurality of sets of visual attention tests to the subject, each test comprising a respective central target and respective peripheral target, each set characterized by an average display time and an average peripheral target eccentricity, said plurality of sets comprising first and second sets;

means for increasing the average peripheral target eccentricity for the first set of tests up a maximum eccentricity when the subjet's success rate in identifying the central targets and locating the peripheral targets in a respective preceding set of tests is above a threshold level; and means for reducing the average peripheral target eccentricity and reducing the average display time for the second set of tests when the average peripheral target eccentricity is at a maximum eccentricity and the subjet's success rate in identifying the central targets and locating the peripheral targets in a respective preceding set of tests is above the threshold level.

24. A computer-readable storage medium comprising a computer program, said program comprising:

means for administering a plurality of sets of visual attention tests to the subject, each test comprising a respective central target and respective peripheral target, each set characterized by an average display time and an average peripheral target eccentricity, said plurality of sets comprising first and second sets;

means for increasing the average peripheral target eccentricity for the first set of tests up a maximum eccentricity when the subjet's success rate in identifying the central targets and locating the peripheral targets in a respective preceding set of tests is above a threshold level; and means for reducing the average peripheral target eccentricity and reducing the average display time for the second set of tests when the average peripheral target eccentricity is at a maximum eccentricity and the subjet's success rate in identifying the central targets and locating the peripheral targets in a respective preceding set of tests is above the threshold level.

25. The invention of claim 18, 19, 20, 21, 23 or 24 wherein the display time is substantially constant within each set.

26. The invention of claim 18, 19, 20, 21, 23 or 24 wherein the peripheral target eccentricity is substantially constant within each set.

27. The invention of claim 18, 19, 20, 21, 23 or 24 wherein both the display time and the peripheral target eccentricity are substantially constant within each set.

* * * * *

UNITED STATES PATENT AND TRADEMARK OFFICE
CERTIFICATE OF CORRECTION

PATENT NO. : 6,364,486 B1
DATED : April 2, 2002
INVENTOR(S) : Karlene K. Ball et al.

It is certified that error appears in the above-identified patent and that said Letters Patent is hereby corrected as shown below:

<u>Column 8,</u>
Line 30, after "comprising" insert -- displaying at least one visual element for a respective limited time period, said --.

<u>Column 9,</u>
Lines 20 and 25, delete "subjet's" and substitute -- subject's -- in its place.

<u>Column 10,</u>
Lines 19 and 26, delete "subjet's" and substitute -- subject's -- in its place.

<u>Column 11,</u>
Lines 3 and 11, delete "subjet's" and substitute -- subject's -- in its place.

<u>Column 12,</u>
Lines 1 and 10, delete "subjet's" and substitute -- subject's -- in its place.

Signed and Sealed this

Twenty-fifth Day of March, 2003

JAMES E. ROGAN
*Director of the United States Patent and Trademark Office*